United States Patent [19]

Franklin et al.

[11] Patent Number: 5,573,755
[45] Date of Patent: Nov. 12, 1996

[54] SUNSCREEN AGENTS

[75] Inventors: Kevin R. Franklin, Merseyside, Great Britain; Charles C. Nunn, Rutherford, N.J.

[73] Assignee: Chesebrough-Pond's USA Co., Division of Conopco, Inc., Greenwich, Conn.

[21] Appl. No.: 289,042

[22] Filed: Aug. 11, 1994

[30] Foreign Application Priority Data

Aug. 13, 1993 [GB] United Kingdom .................. 9316901

[51] Int. Cl.$^6$ .................. A61K 7/42; A61K 31/315; A61K 31/30
[52] U.S. Cl. .................. 424/59; 424/60; 514/494; 514/499; 556/36; 556/37
[58] Field of Search .................. 424/59; 556/37, 556/36

[56] References Cited

U.S. PATENT DOCUMENTS 5,302,376  4/1994  Forestier et al. .................. 424/59

FOREIGN PATENT DOCUMENTS

| | | | |
|---|---|---|---|
| 9-46344/89 | 6/1990 | Australia | 424/59 |
| 0207810 | 11/1988 | European Pat. Off. | 424/59 |
| 0431755 | 6/1991 | European Pat. Off. | A61K 7/42 |
| 0457687 | 11/1991 | European Pat. Off. | A61K 7/42 |
| 9119679 | 12/1991 | WIPO | 424/59 |
| WO92/00355 | 1/1992 | WIPO | C09B 69/10 |
| WO93/10753 | 6/1993 | WIPO | A61K 7/42 |

OTHER PUBLICATIONS

International Search Report in International Patent Application PCT/EP 94/02669, Oct.1994.

Benzekri, A. et al., "Structural, Magnetic, and Redox Properties of Dicopper Complexes of a New Binucleating Ligand Involving Sulphides and Benzimidazoles in Addition to a Phenoxide Bridge" *Journal of the Chemical Society*, (No. 20, Oct. 15, 1987), pp. 1564–1565.

Alzuet, G. et al., "Acetazolamide Binding to Zinc (II), Cobalt (II), and Copper (II) Model Complexes of Carbonic Anhydrase", *Journal of the Chemical Society*, No. 16, (1994), pp. 2347–2351.

International Search Report in European Patent Application PCT/EP 94/02668.

Patent Abstracts of Japan; vol. 10, No. 17 (C–324) (Abstract of JP 60174710).

Patent Abstracts of Japan; vol. 10, No. 17 (C–324) (Abstract of JP 60174711).

Chibwe, Malama. "Synthesis, Characterization and Catalytic Properties of Mixed Metal Oxides". Nov. 1989, p. 95—a pertinent page from a thesis by M. Chibe.

Meyn, Martina et al. "Anion–Exchange Reactions of Layered Double Hydroxides". Inorg. Chem. (1990), vol. 29 pp. 5201–5207.

Miyata, Shigeo. "Anion–Exchange Properties of Hydrotalcite–like Compounds". Clays and Clay Minerals, (1983) vol. 31, No. 4 pp. 305–311.

Derwent Abstract of JP 5001195. Abstract of JP A 10 66 110—Patent Abstracts of Japan, vol. 13, No. 262, Jun. 16, 1989.

Abstract of JP60149515,JP6019515, Aug. 7, 1985, Kanebo.

*Primary Examiner*—Shelley A. Dodson
*Attorney, Agent, or Firm*—Rimma Mitelman

[57] ABSTRACT

Hydroxy salts of formula:

$$[M(OH)_{(2-a)}]^{a+} X^{b-}_{a/b} \cdot zH_2O$$

where M is zinc, copper or a mixture of the two and X denotes anions at least some of which display ultraviolet absorption over at least a portion of the wavelength range from 290 to 400 nanometers, their use as sunscreen agents and sunscreen compositions comprising them together with a cosmetically acceptable vehicle.

8 Claims, No Drawings

SUNSCREEN AGENTS

This invention relates to sunscreen agents, that is to say compounds capable of absorbing ultra violet radiation with a wavelength in the range from 290 to 400 nanometers. The invention also relates to sunscreen compositions for application to human skin incorporating the sunscreen agents.

In general terms, harmful ultra-violet (UV) rays, particularly those originating from sunlight, which penetrate the upper atmosphere and reach the earth's surface, can be classified into:

i. the energy-rich UV-B rays (290–320 nm wavelength) which possess an intense physiopathological activity on the skin; these are absorbed just above the dermis and they are responsible for erythema and skin pigmentation; and ii. UV-A rays (320–400nm wavelength) which penetrate deeper into the skin (to the dermis and beyond). Their energy is much lower and the photobiological effects they cause are much more long term in nature, for example, they accelerate skin ageing.

Sunscreen compositions should desirably provide protection against both UV-A and UV-B rays, but protection against UV-A rays is particularly desirable, in order to prevent the long term photobiological effects resulting from UV-A radiation.

Meyn et al, in Inorganic Chemistry, Vol 32 pages 1209–1215 (1993) have described water-insoluble hydroxy salts which can be represented by a general formula

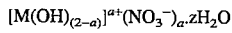

$$[M(OH)_{(2-a)}]^{a+}(NO_3^-)_a \cdot zH_2O$$

where M is a mixture of divalent metals. It is described in this paper that these hydroxy double salts have a layered structure and will undergo ion exchange to replace nitrate ions with organic anions. The metal atoms lie in layers in which metal atoms are connected together through OH groups. The anions project into interlayers between the layers of metal ions.

We have now found that ultraviolet absorbing anions can be introduced into hydroxy salts of this type, and then retain their ultraviolet absorbance.

In a first aspect this invention provides a hydroxy salt of the formula $$[M(OH)_{(2-a)}]^{a+}X^{b-}_{a/b} \cdot zH_2O$$

where M is zinc, copper or a mixture of the two and X denotes anions at least some of which display ultraviolet absorption over at least a portion of the wavelength range from 290 to 400 nanometers.

In a second aspect the invention provides a sunscreen composition for application to human skin comprising a cosmetically acceptable vehicle incorporating a said hydroxy salt in which at least some of the anions X display ultraviolet absorption over at least a portion of the wavelength range from 290 to 400 nanometers.

The invention also relates to the use of such hydroxy salts as sunscreen agents and to prepare sunscreen compositions. The value of z will generally lie in a range from 0 to 10, more preferably 0 to 1.

In general it will be desirable that the ultraviolet absorbing anions have a fairly strong absorption in at least a portion of the stated range from 290 to 400 nanometers. This may be specified as a requirement that the acid form or a simple alkali metal or ammonium salt of the anion exhibits absorption with a molar extinction coefficient of at least $2 \times 10^3$, preferably $3 \times 10^3$, more preferably at least $5 \times 10^3$ and yet more preferably at least $8 \times 10^3$ over at least a portion of the stated wavelength range from 290 to 400nm.

We have found that when such anions are incorporated into a hydroxy salt, their ultraviolet absorption is, in general, retained. However, there is often a broadening of the absorption, leading to enhanced UV-A absorption compared to the UV-A absorption displayed by these anions prior to their incorporation. Thus, in preferred embodiments of the invention, enhanced UV-A protection is attained by virtue of incorporating the anions into a hydroxy salt.

Effective ultraviolet absorption may be provided by an absorption band whose maximum is outside the stated range. For example the p-methoxy cinnamate ion has an absorption maximum at 285 nanometers but the absorption band is broad enough to provide strong absorption over a range from 290 nanometers up to at least around 320 nanometers.

It will often be the case that absorption in the range 290 to 400 nanometers will be provided by an absorption band with a maximum in the range 260 to 360 nanometers.

Preferably the anions do not have strong absorption in the visible band from 400 to 700 nanometers, especially in the part of it from 450 nanometers upwards, notably from 450 or 500 to 650 nanometers. The extinction coefficient for absorption in such ranges may preferably be no greater than $5 \times 10^2$ throughout the ranges concerned.

The molar extinction coefficient of a substance is usually measured in solution and is then given by the formula

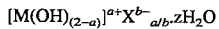

$$\epsilon = \frac{1}{cl} \log_{10} \frac{I_o}{I}$$

where I is the intensity of radiation transmitted through the sample, $I_o$ is the intensity of radiation transmitted through a reference sample consisting of the same solvent but without the substance under test, c is molar concentration in moles/liter, and l is the path length through the solution, in centimeters.

The proportion of anions X which absorb ultraviolet radiation may be fairly small, for example as little as 3 mole %, better at least 5 mole % of all the anions present, but may be higher such as a majority of the anions present and even up to 100%.

The anions which absorb ultraviolet radiation may suitably be one or more of the following:
para amino benzimidazole-5-sulphonate
3-imidazol-4-yl acrylate
salicylate
p-methoxy cinnamate
2 ethyl hexyl-2-cyano-3,3 diphenyl acrylate
3,3,5 trimethylcyclohexyl-2-acetamido benzoate
p-aminobenzoate
cinnamate
3,4-dimethoxy phenyl glyoxylate
α-(2-oxoborn-3-ylidene)-p-xylene-2-sulphonate
α-(2-oxoborn-3-ylidene)toluene-4-sulphonate
α-cyano-4-methoxy cinnamate
2-phenyl benzimidazole-5-sulphonate.

These anions, when in the free state, are known to display absorption in the wave length range from 290 to 400 nanometers. All of them are regarded as acceptable materials to serve as sunscreen agents.

As mentioned above, we have now found that when they are incorporated as anions in a hydroxy salt, their ability to absorb ultraviolet radiation is retained. In most instances, when the above-listed anions are incorporated into a hydroxy salt, there is no major change in the ultraviolet absorption spectrum, although an advantageous enhancement of absorption in the UV-A region may occur.

Another group of organic materials suitable for the purposes of this invention are those which contain weak acid functionality through the inclusion of a phenolic proton or other weakly acidic proton in the molecule. This proton can be removed to form an anion which can be incorporated into a hydroxy salt. The anions derived from such compounds may have absorption spectra significantly different from the parent compound, but nevertheless, these anions, upon incorporation into a hydroxy salt, display significant absorption of light between 290 and 400 nm (UV-A region).

An important group of such phenolic compounds are hydroxylated benzophenone derivatives. Certain diketone compounds which can exist in a weakly acidic enol form may also be included. Examples of such compounds from which anions can be derived include but are not limited to the following materials for which both CTFA and chemical names are given:

| CTFA Name | Chemical Name |
| --- | --- |
| Benzophenone-1 | 2,4-Dihydroxybenzophenone |
| Benzophenone-2 | 2,2',4,4'-Tetrahydroxybenzophenone |
| Benzophenone-3 | 2-Hydroxy-4-methoxy benzophenone |
| Benzophenone-4 | 2-Hydroxy-4-methoxy benzophenone-5-sulphonic acid |
| Benzophenone-5 | 2-Hydroxy-4-methoxy benzophenone-5-sulphonic acid; monosodium salt |
| Benzophenone-6 | 2,2'-Dihydroxy-4,4'-dimethoxy benzophenone |
| Benzophenone-7 | 5-Chloro-2hydroxy benzophenone |
| Benzophenone-8 | 2,2'-Dihydroxy-4-methoxy benzophenone |
| Benzophenone-9 | 2,2'-Dihydroxy-4,4'-dimethoxy benzophenone-3,3'-disulphonic acid; disodium salt |
| Benzophenone-10 | 2-Hydroxy-4-methoxy-4'-methyl benzophenone |
| Benzophenone-12 | 2-Hydroxy-4-octoxy benzophenone |
| Homosalate | Homomenthyl salicylate |
| Octyl Salicylate | 2-ethylhexyl salicylate |

Some tradenames and suppliers are:

| CTFA Name | Trade Name | Supplier |
| --- | --- | --- |
| Benzophenone-1 | UVINUL 400 | BASF Chemical Co. |
| Benzophenone-2 | UVINUL D-50 | BASF Chemical Co. |
| Benzophenone-3 | UVINUL M-40 | BASF Chemical Co. |
| Benzophenone-4 | UVINUL MS-40 | BASF Chemical Co. |
| Benzophenone-5 | | Quest |
| Benzophenone-6 | UVINUL D-49 | BASF Chemical Co. |
| Benzophenone-7 | | Quest |
| Benzophenone-8 | SPECTRA-SORB UV-24 | American Cyanamide |
| Benzophenone-10 | UVISTAT 2211 | Ward Blenkinsop |
| Benzophenone-12 | CYASORB UV531 | American Cyanamide |
| Homosalate | KEMESTER HMS | Hunko Chemical |
| Octyl Salicylate | SUNARONE WMO | Felton Worldwide |

Another compound which can provide anions is Butyl Methoxydibenzoylmethane available as PARSOL 1789 from Givaudan Corp.

Also included in this form of the invention are anionic species derived from Pongomol which is a substituted 1,3-diketone whose systematic name is 1-(4-methoxy-5-benzofuranyl)-3-phenyl-1,3-propanedione. It has an ultra-violet absorption band within the range of from 250 to 500 nm, and an extinction coefficient of from 5,000 to 70,000. The diketone is more fully described in U.S. Pat. No. 5,152,983 incorporated by reference herein.

Among these materials, Benzophenone-4 and Benzophenone-9 have both a strong acid functionality conferred by a sulphonate group and weak acid functionality, conferred by the phenolic proton. For these materials (and for Benzophenone-5 which is the monosodium salt of Benzophenone-4), multiple anionic forms of the material may be produced and incorporated into hydroxy salts. Thus, for example, with Benzophenone-4, both an mono- and dianion can be incorporated into hydroxy salts. Both monoanionic and dianionic forms of this material and any combinations thereof incorporated into hydroxy salts may be useful for sunscreens and are to be considered within the scope of this invention.

Hydroxy salts of this invention are insoluble both in water and in other solvents. They can however be suspended as dispersions in solvents including water. A sunscreen composition according to this invention will therefore have the hydroxy salt, with ultraviolet-absorbing anions, dispersed in the vehicle. Preferably the vehicle is aqueous and the hydroxy salt is suspended in this. For use the composition is rubbed onto skin and the water then evaporates, along with any volatile organic compounds included in the vehicle. This leaves the hydroxy salt as a deposit on the skin. The layer structure of the material assists in the deposition of the material as a continuous layer on the skin.

The aqueous vehicle may be an oil-in-water emulsion with the hydroxy salt suspended in that emulsion. The hydroxy salt may suspend in the aqueous phase of such an emulsion or, less likely, suspend in the oil phase.

Hydroxy salts are insoluble materials and are macromolecules so that the molecular size is large compared with the size of the organic compounds which are conventional sunscreen agents.

These properties are advantageous. Once hydroxy salts have been deposited on the skin, their large molecular size and/or their insolubility means that they should not be prone to penetrating into the skin, nor to moving about on the skin surface. (Penetration into the body through the skin and migration to sensitive areas such as the eyes are both potential hazards with water-soluble sunscreen active agents). Because the materials of the invention are insoluble, they also cannot dissolve away while the user is swimming, which provides a further advantage.

A sunscreen composition containing a hydroxy salt in accordance with this invention can be prepared by adding the hydroxy salt to an aqueous vehicle, which at its simplest may be water alone, and then mixing to form a suspension.

It is envisaged that a sunscreen composition according to this invention will contain from 0.05 to 50% by weight of the hydroxy salt, more preferably from 0.1 to 30% by weight, yet more preferably 2 to 20% by weight. The amount which is incorporated will affect the amount of ultraviolet absorption achieved, of course. Therefore amounts towards the upper end of the range would be used for sunscreen compositions intended to give a high degree of protection against ultraviolet radiation.

Other materials may be included in sunscreen compositions according to this invention. It is within the scope of this invention to incorporate an additional sunscreen agent. Possibilities include nonionic organic sunscreen agents, inorganic sunscreen agents such as finely divided titanium dioxide and particles of organic polymers.

Other materials which may possibly be included in a sunscreen composition include thickening agents, emollient oils, humectants and fluids to enhance lubricity, notably silicone oils. Minor constituents which may be present include perfume and preservatives.

Preparation of a hydroxy salt incorporating ultraviolet absorbing anions will generally take place in two stages: the first stage being the preparation of a hydroxy salt with some other anions and the second stage being ion exchange to replace at least some of the anions with ultraviolet absorbing anions.

The preparation of some hydroxy salts has been described by Meyn et al, as referred to above. We have found it satisfactory to treat suspension of zinc oxide with zinc or copper nitrate, preferably at an elevated temperature, followed by filtering off the solid.

The hydroxy salts can be identified by chemical analysis for the elements present and by X-ray diffraction.

Ion exchange to introduce the ultraviolet absorbing anions can be carried out by suspending a hydroxy salt in an aqueous solution of the anions which it is desired to introduce. The process may be carried out at an elevated temperature to increase the speed of reaction. The hydroxy salt is then filtered off. It can be characterised by chemical analysis and by ultraviolet spectroscopy carried out on an aqueous suspension of the hydroxy salt.

EXAMPLES

Preparation 1

Preparation of Zinc Hydroxy Salt Containing Nitrate Ion 68 g of zinc oxide was suspended in 200 ml of distilled water in a one liter polypropylene screwcap bottle. 250 g of zinc nitrate were dissolved in 400 ml of distilled water and the resulting solution was added, with stirring, to the zinc oxide suspension. The bottle was capped, shaken vigorously for 2 minutes and then placed in a thermostated oven for 23 hours at 90° C. At the end of this period the solid was filtered off, washed thoroughly with water and then freeze dried. The dried material was finally equilibrated with water vapour by storing in a desiccator over a saturated sodium chloride solution.

The composition of this material was determined by thermal and chemical analysis. The results were as follows:
% Zn=58.3%
% N=2.12%
% hydration water=3.65%

This is consistent with a formula

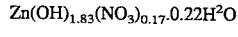

$Zn(OH)_{1.83}(NO_3)_{0.17}.0.22H^2O$

The X-ray powder diffraction pattern of this material showed characteristic major peaks at 9.8A and 4.9A.

Scanning electron microscopy showed the product to be composed of plate crystals of 1–2 μm diameter.

The uv spectrum of a suspension of 50 mg/liter of the material in water, measured over the range 250 to 450 nm showed no appreciable absorption bands.

Example 1

Ion-exchange of 4-Methoxy Cinnamate Anion into Zinc Hydroxy Salt 5.71 g of 4-methoxy cinnamic acid and 1.28 g of sodium hydroxide were dissolved in 200 ml of water. This solution was added to 10 g of the product from Preparation 1 in a polypropylene screwcap bottle. The bottle was capped, shaken for 2 minutes, and then heated at 90° C. for 18 hours. The solid was filtered off, washed with warm water and then oven dried at 90° C.

Chemical analysis showed that the product contained 26.0% by weight of 4-methoxy cinnamate ions.

The X-ray diffraction pattern of the product showed
 i) the characteristic peaks of the starting material were absent.
 ii) there were three new peaks at 27A, 13.5A and 9,0A which were not present in the starting material.

The uv spectrum of a suspension of 50 mg/liter of the material in water, showed a broad peak centred at 286 nm with a tail extending to at least 400 nm. The absorbance at 360 nm was 19% of the absorbance at 286 nm, whereas for sodium methoxycinnamate the absorbance at 360 nm is less than 0.2% of the absorbance at 286 nm.

Example 2

Ion-exchange of p-aminobenzoate into Zinc Hydroxy Salt 4.4 g of p-amino benzoic acid and 1.28 g of sodium hydroxide were dissolved in 200 ml of water and solution added to 10 g of the product from Preparation 1. The suspension was then heated in a capped polypropylene bottle for 18 hours at 90° C. The solid product was filtered off, washed with warm water, and then oven dried at 90° C.

X-ray powder diffraction of the product showed the two characteristic peaks within the starting material were absent but that new peaks, characteristic of the p-amino benzoate containing material, were present at 24A, 12A and 8A. The X-ray powder diffraction pattern also showed the product contained some zinc oxide.

Chemical analysis showed the product contained 6.28% by weight p-amino benzoate.

The uv spectrum of a suspension containing 50 mg/l of the product in water showed a broad adsorption peak centred at 265 nm and with a tail extending to at least 330 nm. The absorbance at 330 nm was 29.8% of the absorbance at 265 nm, whereas for sodium p-aminobenzoate the absorbance at 330 nm is less than 0.2% of the absorbance at 265 nm.

Preparation 2

Preparation of a Zinc/Copper Hydroxy Salt Containing Nitrate Ion 72.48 g of $Cu(NO_3)_2.3H_2O$ were dissolved in 300 ml of water and added to a slurry of 29.4 g ZnO in 50 m of water. The mixture was shaken in a capped polypropylene bottle for 2 minutes and then heated at 90° C. for 48 hours. The solid product was filtered off washed with warm water and then freeze dried.

X-ray powder diffraction pattern of the product showed major peaks at 6.9A and 4.45A which are characteristic of this material.

Scanning electron microscope imaging showed the product to be composed of 0.2 to 0.4 um diameter plate crystals.

Thermal and chemical analysis yielded the following chemical data
% Zn=21.8%
% Cu=31.4%
% N=4.78%
% hydration water=<0.2%

This is consistent with the chemical composition $$Zn_{0.4}Cu_{0.6}(OH)_{1.58}(NO_3)_{0.42}$$

The uv absorption spectrum of a 50 mg/l suspension of the product in water showed no appreciable absorption bands in the region 250 to 450 nm.

Example 3

Ion-exchange of 4-methoxy Cinnamate into Zinc/Copper Hydroxy Salt 5.71 g of 4-methoxy cinnamic acid and 1.28 g of sodium hydroxide were dissolved in 200 ml of water and the solution added to 10 g of the product from Preparation 2. The suspension was then heated in a capped polypropylene bottle for 18 hours at 90° C. The solid product was filtered off, washed with warm water, and then oven dried at 90° C.

X-ray powder diffraction of the product showed that the two characteristic peaks of the starting material were still present, but were greatly diminished in intensity. New peaks, characteristic of the 4-methyoxy cinnamate-containing Zn/Cu hydroxy material, were also present at 23A, 11.5A, and 7.7A.

Chemical analysis showed the product contained 43.07% by weight 4-methoxy cinnamate. This is consistent with the chemical composition $$Zn_{0.4}Cu_{0.6}(OH)_{1.58}(mcin)_{0.39}(NO_3)_{0.03}$$

where mcin=4-methoxy cinnamate.

The uv spectrum of a suspension containing 50 mg/l of the product in water showed a broad adsorption peak centred at 286 nm with a tail extending to at least 400 nm. The absorbance at 360 nm was 15.9% of the absorbance at 286 nm, whereas for sodium methoxycinnamate the absorbance at 360 nm is less than 0.2% of the absorbance at 286 nm.

Example 4

Ion-exchange of 2-Phenylbenzimidazole-5-sulphonate Into Zinc/Copper Hydroxy Salt 8.8 g of 2-Phenylbenzimidazole-5-sulphonic acid and 1.28 g of sodium hydroxide were dissolved in 200 ml of water and the solution added to 10 g of the product from Preparation 2. The suspension was then heated in a capped polypropylene bottle for 18 hours at 90° C. The solid product was filtered off, washed with warm water, and then oven dried at 90° C.

X-ray powder diffraction of the product showed that the two characteristic peaks within the starting material were still present, but were diminished in intensity. New peaks, characteristic of the product containing 2-Phenylbenzimidazole-5-sulphonate were also present at 21.3A and 10.7.

Chemical analysis showed the product contained 11.9% by weight 2-Phenylbenzimidazole-5-sulphonate. This is consistent with the chemical composition.

$$Zn_{0.4}Cu_{0.6}(OH)_{1.58}(pbs)_{0.06}(NO_3)_{0.36}$$

where pbs=2-Phenylbenzimidazole-5-sulphonate.

The uv spectrum of a suspension containing 50 mg/l of the product in water showed a broad adsorption peak centred at 302 nm with a tail extending to at least 400 nm. The absorbance at 360 nm was 27% of the absorbance at 302 nm, whereas for sodium 2-phenylbenzimidazole-5-sulphonate the absorbance at 360 nm is less than 0.2% of the absorbance at 302 nm.

Example 5

Ion-exchange of a 2-Hydroxy-4-methoxy benzophenone-5-sulphonate into Zinc/Copper Hydroxy Salt 9.89 g of 2-Hydroxy-4-methoxy benzophenone-5-sulphonic acid and 1.28 g of sodium hydroxide were dissolved in 200 ml of water and the solution added to 10 g of the product from Preparation 2. The suspension was then heated in a capped polypropylene bottle for 18 hours at 90° C. The solid product was filtered off, washed with warm water, and then oven dried at 90° C.

X-ray powder diffraction of the product showed the two characteristic peaks within the starting material were still present, but were diminished in intensity. A new peak, characteristic of the product containing 2-Hydroxy-4-methoxy benzophenone-5-sulphonate was also present at 22A.

Chemical analysis showed the product contained 3.1% by weight 2-Hydroxy-4-methoxy benzophenone-5-sulphonate.

The uv spectrum of a suspension containing 50 mg/l of the product in water showed a broad adsorption band centred at 290 nm and with a tail extending to at least 400 nm. The absorbance at 360 nm was 37% of the absorbance at 290 nm, whereas for the monosodium salt of 2-hydroxy-4-methoxy benzophenone-5-sulphonic acid the absorbance at 360 nm is less than 14% of the absorbance at 290 nm.

Example 6

The following formulations were prepared.

| | WT. % | INGREDIENT |
|---|---|---|
| Phase A | 75.9% | Water |
| Phase B: | 5% | Zinc hydroxy salt of 4-methoxycinnamate (Example 1) |
| | 10% | Finsolv |
| | 1% | Brij 72 |
| | 4% | Brij 721 |
| Phase C: | 1% | Xanthan Gum |
| | 3% | Propylene glycol |
| Phase D: | 0.1% | Glydant plus |

The process for formulation was

Heat Phase B to 80° C. and homogenise. Heat Phase A to 80° C. and then slowly add Phase B while stirring. Add in Phase C and then cool to 40° C. and add Phase D.

We claim:

1. Hydroxy salt of the formula $$[M(OH)_{(2-a)}]^{a+}X^{b-}{}_{a/b}.zH_2O$$

wherein M is Zn, Cu or a combination of both, and X denotes anions at least some of which display ultraviolet absorption over at least a portion of the wavelength range from 290 to 400 nanometers.

2. Hydroxy salt according to claim 1 wherein at least some of the anions X display ultraviolet absorption with a molar extinction coefficient of at least $2 \times 10^3$ over at least a portion of the wavelength range from 290 to 400 nanometers.

3. Hydroxy salt according to claim 1 wherein at least 5 mole % of the anions X are the anions of one or more of para amino benzimidazole-5-sulphonate
3-imidazol-4-ylacrylate
salicylate
p-methoxy cinnamate
2 ethyl hexyl-2-cyano-3,3 diphenyl acrylate
3,3,5 trimethylcyclohexyl-2-acetamido benzoate
cinnamate
p-aminobenzoate
3,4-dimethoxy phenyl glyoxylate
α-(2-oxoborn-3-ylidene)-p-xylene-2-sulphonate
α-(2-oxoborn-3-ylidene)toluene-4-sulphonate
α-cyano-4-methoxy cinnamate
2-phenyl benzimidazole-5-sulphonate.

4. Hydroxy salt according to claim 1 wherein at least 5 mole % of the anions X are anions of phenolic compounds, especially compounds comprising a hydroxylated benzophenone moiety, which display ultraviolet absorption over at least a portion of the wavelength range from 200 to 400 nm.

5. Hydroxy salt according to claim 4 wherein at least 5 mole % of the anions X are anions of one or more of:
Benzophenone-1
Benzophenone-2
Benzophenone-3
Benzophenone-4
Benzophenone-5
Benzophenone-6
Benzophenone-7
Benzophenone-8
Benzophenone-9
Benzophenone-10
Benzophenone-12
butyl methoxydibenzoylmethane
1-(4-methoxy-5-benzofuranyl)-3-phenyl-1,3-propanedione
homomenthyl salicylate, or
2-ethylhexyl salicylate.

6. Hydroxy salt according to claim 1 wherein at least a majority of the anions X are anions of any of the compounds named in claims 3 and 5.

7. Hydroxy salt according to claim 1 wherein a majority of the anions X display a molar extinction coefficient of at least $5 \times 10^3$.

8. A sunscreen composition for application to human skin comprising a cosmetically acceptable vehicle incorporating one or more hydroxy salts according to claim 1.

* * * * *